US00PP31426P2

(12) United States Plant Patent
Austin

(10) Patent No.: US PP31,426 P2
(45) Date of Patent: Feb. 4, 2020

(54) ***ROSA HYBRIDA* SHRUB NAMED 'AUSTULLIVER'**

(50) Latin Name: *Rosa hybrida*
Varietal Denomination: AUStulliver

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/350,906

(22) Filed: Jan. 30, 2019

(30) Foreign Application Priority Data

Sep. 21, 2018 (GB) ..... PBR 5/2138

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./107
CPC ..... A01H 5/02; A01H 6/74
See application file for complete search history.

*Primary Examiner* — Annette H Para
(74) *Attorney, Agent, or Firm* — KPPB LLP

(57) ABSTRACT

A variety of rose plant of the shrub class, named 'AUStulliver'. The 'AUStulliver' is a variety of a rose shrub having a slightly arching growth with large clusters of neat, deeply-cupped blooms held above glossy foliage that are initially mid-pink and that pale as they open with individual petals having a darker pink edge revealing a small boss of stamens, and having a sweet fruity fragrance.

1 Drawing Sheet

Classification: The present invention relates to a new *Rosa hybrida* shrub of the market class 'English Rose'.

Variety denomination: The new plant has the varietal denomination 'AUStulliver'.

CROSS-REFERENCE TO RELATED APPLICATION

The present application claims priority to UK Varietal Plant Patent 5/2138, filed Sep. 21, 2018.

ORIGIN OF INVENTION

This invention relates to a new and distinct variety of shrub rose plant named 'AUStulliver', which was originated from the cross-pollination of the two 'unnamed' and unpatented seedlings of *Rosa hybrida.*

BACKGROUND OF THE INVENTION

The primary objective of this breeding was to produce a bushy rose variety having a slightly arching growth with large clusters of neat, deeply-cupped blooms held above glossy foliage that are initially mid-pink and that pale as they open with individual petals having a darker pink edge revealing a small boss of stamens, and having a sweet fruity fragrance.

SUMMARY OF THE INVENTION

Among the features which distinguish the new variety from others presently available and commercial rose cultivars known to the inventor is the following combination of characteristics: a bushy, arching growth that has glossy foliage and is highly disease resistant and having neat, deeply-cupped blooms held in large clusters with a sweet fruity fragrance.

Asexual reproduction of the new variety by budding as performed at Bowling Green Lane in Albrighton, Britain shows that the foregoing and other distinguishing characteristics come true to form and are established and transmitted through succeeding asexual propagations. 'AUStulliver' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUStulliver' are two unnamed seedlings. The new rose may be distinguished from its maternal parent, by the following combination of characteristics: the maternal parent has flatter, rosette-shaped flowers and a stiffer growth that is less disease resistant than 'AUStulliver'. The new rose may be distinguished from its paternal parent, by the following combination of characteristics: the paternal parent has single flowers and is much taller than 'AUStulliver'.

COMPARISON WITH THE CLOSEST COMMERCIALLY AVAILABLE CULTIVAR

The closest commercially available cultivar to the new variety is the 'AUSrumba' (U.S. Plant Pat. No. 17,500). The bloom form of 'AUSrumba' is a shallow cup with a broader bloom, whereas 'AUStulliver' has a deeper cup with smaller breadth. The petal color of 'AUSrumba' is blush pink, whereas 'AUStulliver' is a pale pink with deeper pink on the edges. The foliage of 'AUSrumba' is matt, whereas 'AUStulliver' is glossy. Another similar variety is 'AUSbreeze'

(U.S. Plant Pat. No. 20,962), but while the pink color of both is similar, 'AUSbreeze' does not have the dark pink edge to the petals displayed in 'AUStulliver'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUStulliver' specimens were made at the nursery at David Austin Roses Limited in Albrighton, Wolverhampton, United Kingdom. The following description is of 5 year-old rose plants of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.5 cm long and 1.8 cm in diameter when the petals start to unfurl.

*Form*.—The bud form is pointed ovoid and broad-based.

*Color*.—When sepals first divide, the bud color is RHS 36C (red group) with RHS 58C (red-purple group). When half blown, the upper sides of the petals are RHS 36C (red group), and the lower sides of the petals RHS 36C (red group) and RHS 58C (red-purple group).

*Calyx*.—Shape: opens to a star shape, with the sepals folding back against the stems. Length: 3 cm. Diameter: 1.3 cm.

*Sepals*.—Arrangement: Regularly arranged. Color: Upper Surface: RHS 191B (grayed-green group). Lower Surface: RHS 146A (yellow-green group) with RHS 184B (grayed-purple group). Length: 3 cm. Width: 1 cm. Shape: Lanceolate. Surface texture: Upper Surface: Downy. Lower Surface: Smooth. Number: There are 3 normally appendaged sepals, and 2 unappendaged sepals with hairy edges. Sepal Extensions: Are medium.

*Receptacles*.—Color: RHS 146B (yellow-green group) with RHS 184B (grayed-purple group). Shape: Apple. Size: Medium, about 1.2 cm long×0.9 cm wide. Surface: Smooth.

*Peduncle*.—Length: Medium, averaging about 12 cm. Surface: Smooth. Color: RHS 146B (yellow-green group) with some RHS 184B (grayed-purple group). Strength: Normal.

Blooms:

*Size*.—Medium, average open diameter is about 7 cm.

*Borne*.—In clusters of approximately 10-15 blooms, the inflorescence having a rounded shape.

*Stems*.—Strength: Normal, average length is about 80 cm. Diameter: 6 mm.

*Form*.—When first open, bloom is cupped. Permanence of bloom: retains its form to the end.

*Flower type*.—Double.

Petalage: Number of petals under normal conditions: 100.

*Color*.—The upper sides of the petals are RHS 69C (red-purple group) with a darker pink edge of RHS 68A (red-purple group). The reverse sides of the petals are RHS 69C (red-purple group) with a darker pink edge of RHS 68A (red-purple group). The base of the petals has a yellow spot RHS 4C (yellow group).

*Variegations*.—None.

*Discoloration*.—The general tonality at the end of the first day is RHS 68A (red-purple group), and at the end of the third day is RHS 69C (red-purple group).

*Fragrance*.—Moderate. Character of fragrance: Fruity.

Petals:

*Texture*.—Smooth.

*Size*.—Width: 2.5 cm. Length: 3.4 cm.

*Surface*.—Smooth.

*Shape*.—Obovate.

*Margin*.—Entire with medium undulations and reflexing.

*Apex shape*.—Rounded.

*Base shape*.—Acute.

*Form*.—Incurved.

*Arrangement*.—Regular, with a button eye.

*Petaloids*.—Number: 15-20. Color: RHS 69C (red-purple group). Length: 2 cm. Width: 0.6 cm. Shape: As petal shape but deformed to varying degrees. Margin: Entire.

*Persistence*.—Petals drop off cleanly before drying.

*Lastingness*.—On the plant: Fair about 5 days. As a cut flower: not tested.

Reproductive parts:

*Stamens*.—Number: approximately 6-10. Length: 6 mm.

*Anthers*.—Length: 2 mm. Color: RHS 13B (yellow-orange group). Arrangement: Mixed with petaloids.

*Filaments*.—Color: RHS 17A (yellow-orange group). Length: 4 mm.

*Pollen*.—Color: RHS 17A (yellow-orange group). Amount: Scarce.

*Pistils*.—Number: Approximately 40. Length: 8 mm.

*Styles*.—Color: RHS 38B (red group). Length: 7 mm.

*Stigmas*.—Color: RHS 22A (yellow-orange group). Length: approximately 7 mm.

*Hips*.—NONE Observed.

PLANT CHARACTERISTICS

Plant form: Shrub.

Plant growth: Vigorous and semi-upright.

Age to maturity: 2 years.

Mature plant: Height: 140 cm. Width: 120 cm.

Rootstock: *Rosa dumetorum* 'Laxa' for the observed plants.

Foliage:

*Number*.—Leaflets on normal mid-stem leaves is: 5 (including terminal leaflet).

*Size*.—Large, about 18.5 cm long×14 cm wide.

*Quantity*.—Normal. Number of leaves per flowering stem is: 10.

*Color*.—New foliage: Upper side: RHS 146A (yellow-green group). Lower side: RHS 146B (yellow-green group) with RHS 184B (grayed-purple group). Old foliage: Upper side: RHS 137A (green group). Lower side: RHS 146B (yellow-green group).

Leaflets:

*Size*.—About 8 cm long×4.8 cm wide.

*Shape*.—Pointed oval.

*Base shape*.—Rounded.

*Apex shape*.—Acuminate.

*Texture*.—Leathery.

*Glossiness*.—Strong

*Edge*.—Serrated.

*Serrations*.—Single.

*Petiole*.—Color: RHS 148A (yellow-green group). Length: 5 cm. Width: 2 mm. Surface Texture: Slightly glandular.

*Petiole rachis*.—Color: RHS 148A (yellow-green group). Underside: with prickles.

*Stipules*.—Length: 3.3 cm, glandular. Color: RHS 146A (yellow-green group).

*Auricle*.—Shape: Lanceolate. Length: 1 cm. Width: 1-2 mm. Color: RHS 146A (yellow-green group).

*Vein color*.—Color: RHS 137A (green group).

*Venation pattern*.—Reticulate.

Wood:

*New wood*.—Color: RHS 184B (grayed-purple group). Bark: Smooth.

*Old wood*.—Color: RHS 146A (yellow-green group). Bark: Smooth.

Branching habit:

*Number*.—5.

*Dimensions*.—Length: 90 cm. Diameter: 8 mm.

Stems:

*Mature stem*.—Length: 90 cm. Diameter: 8 mm.

*Internode distance*.—9 cm. The above measurements are all variable, depending on growing conditions in a season.

*Stem pubescence present*.—No.

Prickles:

*Quantity*.—On main canes from base: Few. Number per stem length: 12 per 20 cm mainly in bottom third of stem. On laterals from main canes: Few. Number per stem length: 10 per 20 cm mainly in bottom third of stem.

*Form*.—Deep concave.

*Length*.—4 mm.

*Color when young*.—RHS 184B (grayed-purple group).

*Color when mature*.—RHS 177B (grayed-orange group).

Small prickles:

*Quantity*.—Main stalk: None. Laterals: None.

Disease resistance:

*Powdery mildew* (*Podosphaera pannosa*).—Resistant.

*Downy mildew* (*Peronospora species*).—Resistant.

*Blackspot* (*Diplocarpon rosae*).—Resistant.

*Rust* (*Phragmidium tuberculatum*).—Resistant.

Pest resistance: Not tested.

Winter hardiness: Not tested.

What is claimed is:

1. A new and distinct variety of rose plant of the shrub class, substantially as herein shown and described.

* * * * *

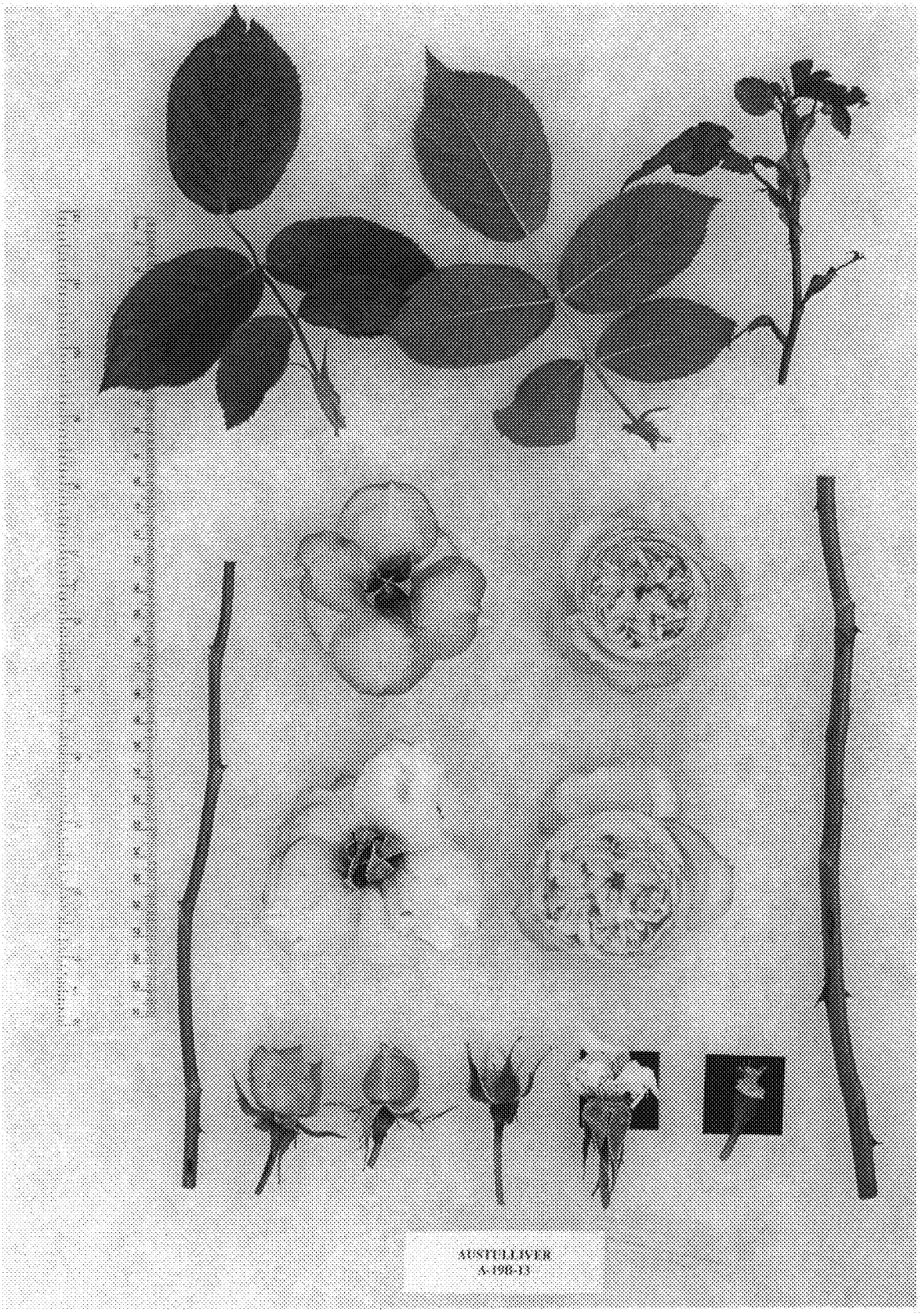
AUSTFLLIVER
A-198-13